United States Patent [19]
Karol et al.

[11] Patent Number: 4,501,597
[45] Date of Patent: * Feb. 26, 1985

[54] DETERGENT FUEL COMPOSITION CONTAINING ALKENYLSUCCINIMIDE OXAMIDES

[75] Inventors: Thomas J. Karol, Wappingers Falls; Rodney L. Sung, Fishkill, both of N.Y.

[73] Assignee: Texaco Inc., White Plains, N.Y.

[*] Notice: The portion of the term of this patent subsequent to Jul. 17, 2001 has been disclaimed.

[21] Appl. No.: 627,134

[22] Filed: Jul. 2, 1984

[51] Int. Cl.³ .................................................. C10L 1/22
[52] U.S. Cl. .................................... 44/63; 252/403
[58] Field of Search ....................... 44/63; 544/379; 252/403

[56] References Cited

U.S. PATENT DOCUMENTS

| | | | |
|---|---|---|---|
| 3,185,704 | 5/1965 | Kahn et al. | 44/63 |
| 3,401,118 | 9/1968 | Benoit, Jr. | 44/63 |
| 3,443,918 | 5/1969 | Kautsky et al. | 44/63 |
| 3,452,002 | 6/1969 | Brasch | 44/63 |
| 3,455,832 | 7/1969 | Davis | 44/63 |
| 3,458,530 | 7/1969 | Siegel et al. | 44/63 |
| 4,257,780 | 3/1981 | Sung et al. | 44/63 |
| 4,313,738 | 2/1982 | Parlman et al. | 44/63 |
| 4,460,381 | 7/1984 | Karol et al. | 44/63 |

*Primary Examiner*—Y. Harris-Smith
*Attorney, Agent, or Firm*—Robert A. Kulason; James J. O'Loughlin; Albert Brent

[57] ABSTRACT

The detergent properties of a motor fuel are improved by incorporating therein a minor amount of a succinimide oxamide prepared by reacting a polyalkyleneamine succinimide with an amount of oxalic acid sufficient to react with at least 30 percent of the reactive nitrogen moieties on the succinimide chain.

7 Claims, No Drawings

DETERGENT FUEL COMPOSITION CONTAINING ALKENYLSUCCINIMIDE OXAMIDES

BACKGROUND OF THE INVENTION

1. Field of the Invention

This invention relates to fuels for internal combustion engines and more particularly to the provision of a novel additive for such fuels.

As is well known, hydrocarbon fuels have a tendency to form polymeric materials (variously called "gum" or "sludge" or "varnish") in various parts of fuel systems. These resin-like deposits tend to form in the fuel supply lines, fuel filter, carburetor, fuel control injectors, intake manifold and valve stems. Such deposits are objectionable not only because of their effect on mechanical performance but also because they decrease the breathing efficiency in engines of the spark ignition type.

Although each type of fuel is composed essentially of hydrocarbons their stability characteristics differ considerably. Thus, typical automotive fuels contain straight and branched chain compounds while aircraft fuels contain a smaller proportion of olefins. Currently, certain types of fuels contain increased amounts of cracked stocks resulting in a higher olefin content and increased susceptibility to the formation of gum.

2. Background of the Invention

The field of this invention evidences considerable research interest. U.S. Pat. No. 3,415,750; Great Britain Pat. No. 1,162,436; U.S. Pat. No. 3,873,460 and coassigned U.S. Pat. Nos. 4,048,080; 4,266,944; and 4,321,062 disclose various classes of chemicals having utility detergents or dispersants in lubricating oil compositions.

The compounds used herein as carburetor detergents are disclosed and claimed in co-pending application Ser. No. 495,295, filed May 16, 1983. Said application is incorporated herein by reference.

SUMMARY OF THE INVENTION

In accordance with the invention there is provided a motor fuel composition comprising a mixture of hydrocarbons in the gasoline boiling range containing an effective detergent amount of detergent compound of the formula selected from the group consisting of I, II, and mixtures thereof, in which R is a hydrocarbyl radical having from 8 to 400 carbon atoms, x and y are numbers which range from 0 to 6 whose additive total is from 1 to 6 and which can be the same or different, R' is a hydrogen radical or a mono- or bi-acyl radical of oxalic acid, and R" is a hydrogen or hydrocarbyl substituted succinic-N-ethylene radical of the formula:

Wherein from about 40 to 100 wt.%, such as 50 to 80 wt.%, of said detergent compound is the oxalic acid derivative of mono-succinimide and the remainder if any, comprises the oxalic acid derivative of bis-succinimide.

These detergent compounds are soluble and/or stable dispersible in liquid hydrocarbon fuels to an extent which allows them to fulfill their function.

This invention also provides a process for operating an internal combustion engine supplying thereto and combusting therein the above motor fuel composition.

DISCLOSURE OF THE INVENTION

The detergency of any gasoline suitable for a spark-ignited internal combustion engine can be improved in the practice of this invention. In general, the base fuel will consist of a mixture of hydrocarbons in the gasoline boiling range i.e., boiling from about 75° to 450° F. The hydrocarbon components can consist of paraffinic, naphthenic, aromatic and olefinic hydrocarbons. This gasoline can be obtained naturally or it can be produced by thermal or catalytic cracking and/or reforming of petroleum hydrocarbons. The base fuel will generally have a Research Octane Number above 85 and up to about 102 with the preferred range being from about 90 to 100.

Effective detergent amounts of detergent compound may be in the range of about 10 to 200 PTB (pounds per thousand barrels), such as about 15 to 75 PTB. Alternatively, the fuel composition may contain from about 0.01 to 10 weight percent, such as about 0.56 to 5.0 wt.%, of said detergent compound.

The fuel composition of this invention comprises a mixture of hydrocarbons boiling in the gasoline boiling range and containing an effective detergent amount of detergent compound of the formula selected from the group consisting of I, II, and mixtures thereof,

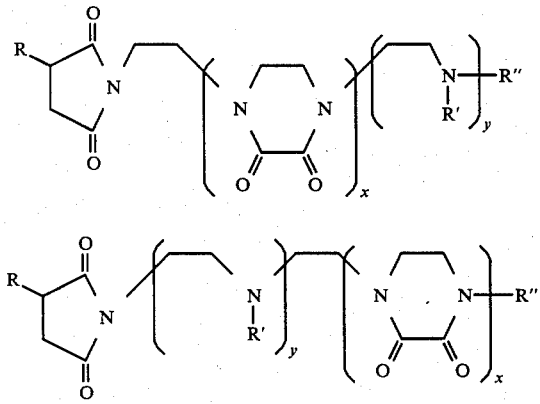

in which R is a hydrocarbyl radical having from 8 to 400 carbon atoms, x and y are numbers which range from 0 to 6 whose additive total is from 1 to 6 and which can be the same or different, R' is a hydrogen radical or a mono- or bi-acyl radical of oxalic acid, and R" is a hydrogen or hydrocarbyl substituted succinic-N-ethylene radical of the formula:

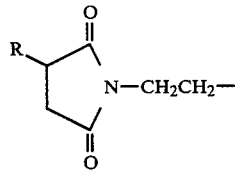

Wherein from about 40 to 100 wt%, such as about 50 to 80 wt% of said detergent compound is the oxalic acid derivative of mono-succinimide and the remainder, if any, comprises the oxalic acid derivative of bis-succinimide.

In various embodiments of the aforesaid structural formulas I and/or II, R may be an alkyl or alkenyl group having from 50 to about 200 carbon atoms; and R may be polyisobutenyl and have a molecular weight of about 1300.

The novel hydrocarbyl-substituted mono- and bis-succinimide oxamides as represented by structural formulas I and/or II, are obtained by reacting at a temperature of about 110° to about 130° C. an alkenyl succinic anhydride, wherein the alkenyl group has from about 8 to 400 carbon atoms, with a polyamine having from about 3 to 20 carbon atoms and from 2 to 10 nitrogen atoms; and wherein the mole ratio of the polyamine to anhydride is from about 0.3:1 to 1.3:1. The resulting succinimide is then reacted with oxalic acid at a temperature in the range of about 150° to about 170° C. It is essential that at least 30 percent, such as 50 to 100 percent of the reactive nitrogen moieties in the succinimide chain of the precursor react with oxalic acid to form the oxamides. Formulation of the resulting detergent compound with motor oil are compatible with engine seals made from synthetic rubber.

The detergent compositions representative of this invention in admixture with the base fuel are referred to herein as the additive fuel and were tested for effectiveness in a carburetor detergency test. This test is run on a Chevrolet V-8 engine mounted on a test stand using a modified four-barrel carburetor. The two secondary barrels of the carburetor are sealed and the feed to each of the primary barrels arranged so that the detergent additive fuel can run in one barrel and the reference fuel run in the other. The primary carburetor barrels were also modified to contain removable aluminum inserts in the throttle plate area so that the deposits formed on the inserts could be conveniently weighed.

In the procedure designed to determine the effectiveness of the additive fuel to remove preformed deposits in the carburetor, first the engine is run for a period of time, usually 24 to 48 hours, using the base test fuel without an additive as the feed to both barrels and with engine blow-by circulated to the air inlet of the carburetor. The weight of the deposits on both of the right and left (R, L) sleeves is then determined and recorded. The engine is then cycled for 24 additional hours with a reference fuel containing a commercial detergent being fed to one barrel, the additive fuel containing the detergent additive of this invention to the other, and no blow-by to the carburetor air inlet. The reference fuel contains 60 PTB (pounds per thousand barrel) of a commercially available carburetor detergent, such as Petrox-1064. Petrox-1064 is a mixture of substituted amines and imides. It is manufactured and sold by Texaco, Inc.

The additive fuel contains 20 PTB by weight of the detergent additive of this invention. The inserts are then removed from the carburetor and weighed to determine the difference between the performance of the additive fuel and the reference fuel in removing the preformed deposits. After the aluminum inserts are cleaned, they are replaced in the carburetor and the process repeated with the fuels reversed in the carburetor to minimize differences in fuel distribution and barrel construction. The effectiveness of the additive fuel is indicated by the difference between deposit removed by the additive fuel containing the detergent of this invention and the reference fuel containing the commercial detergent.

EXAMPLE I

The base test fuel employed in this example was a premium grade gasoline having a Research Octane Number of about 94.3 This gasoline consisted of about 28 percent aromatic hydrocarbons, 11.5 percent olefinic hydrocarbons and 60 percent paraffinic hydrocarbons and boiled in the range from about 90° F. to 380° F. Run Numbers 1, 3, 5, 7, 9 and 11 were made with no detergent in the base test fuel.

The reference fuel used in this example as a standard for comparison purposes was a commercial high octane premium gasoline containing a highly effective carburetor detergent, e.g. Petrox-1064. The additive fuel composition representative of the invention consisted of a mixture of the Base Test Fuel described above containing 20 PTB of the detergent additive of the invention. The base test fuel was mixed with the following detergent additives: Run No. 2 detergent A was 100 wt% of the oxalic acid derivative of mono-succinimide; Run No. 6, detergent B was 100 wt% of the oxalic acid derivative of bis-succinimides; and Run No. 10, detergent C was equal parts of the oxalic acid derivatives of mono and bis-succinimides.

The results of the Chevrolet Carburetor Detergency Test are set forth in Table I below.

TABLE I

| Run | Fuel Composition | Sleeve | Deposit Build-up Mg | Deposit Removed Mg |
|---|---|---|---|---|
| 1 | Base Test Fuel | R | 8.6 | — |
|  |  | L | 10.1 | — |
| 2 | Base Test Fuel and Detergent A (100 wt % Mono-) | R | — | 0.3 |
|  |  | L | — | 3.7 |
| 3 | Base Test Fuel | R | 7.8 | — |
|  |  | L | 12.2 | — |
| 4 | Reference Fuel Containing Petrox-1064 | R | — | 2.7 |
|  |  | L | — | 1.6 |
| 5 | Base Test Fuel | R | 3.0 | — |
|  |  | L | 3.4 | — |
| 6 | Base Test Fuel and Detergent B (100 wt % Bis-) | R | — | 2.0 |
|  |  | L | — | 2.1 |
| 7 | Base Test Fuel | R | 3.4 | — |
|  |  | L | 4.8 | — |
| 8 | Reference Fuel Containing Petrox-1064 | R | — | 2.2 |
|  |  | L | — | 4.5 |
| 9 | Base Test Fuel | R | 3.6 | — |
|  |  | L | 3.5 | — |
| 10 | Base Test Fuel and Detergent C (50 wt % Mono/50 wt % Bis) | R | — | 2.1 |
|  |  | L | — | 3.0 |

TABLE I-continued

| Run | Fuel Composition | Sleeve | Deposit Build-up Mg | Deposit Removed Mg |
|---|---|---|---|---|
| 11 | Base Test Fuel | R | 3.4 | — |
|  |  | L | 5.4 | — |
| 12 | Reference Fuel Containing Petrox-1064 | R | — | 2.7 |
|  |  | L | — | 3.8 |

Substantially equivalent results may be obtained with the detergent compounds tabulated below in Table II.

TABLE II

| R | X | Y | R' | R" |
|---|---|---|---|---|
| 16 carbon atoms | 0 | 6 | H | H |
| 32 carbon atoms | 6 | 0 | H | H |
| 200 carbon atoms | 3 | 3 | mono-oxayl | alkenyl succinyl-N-ethylenyl |
| 10400 carbon atoms | 2 | 4 | bis-oxalyl | alkenyl succinyl-N-ethylenyl |
| 8 carbon atoms | 5 | 1 | mono-oxayl | H |

Mixtures of these compounds are also effective for the stated purposes of the invention.

The foregoing tests show that there are only minor differences between the additive of our invention and the commercial detergent Petrox-1064. However, there is a great economic advantage for the carburetor detergent of our invention. It is less costly and only small concentrations are required to be outstandingly effective. Further, the blended gasoline compositions containing the prescribed novel additive of our invention possess a high level of carburetor detergency properties.

While this invention has been described with reference to various specific examples and embodiments, it is understood that the invention is not limited thereto and that it can be variously practiced within the scope of the following claims.

We claim:

1. A fuel composition comprising a mixture of hydrocarbons boiling in the gasoline boiling range and containing an effective detergent amount of detergent compound of the formula selected from the group consisting of I, II, and mixtures thereof,

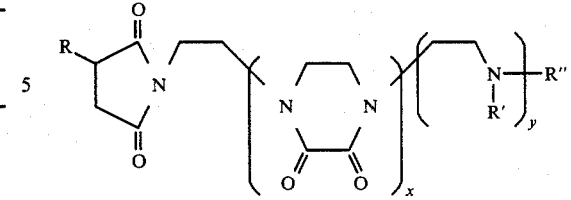

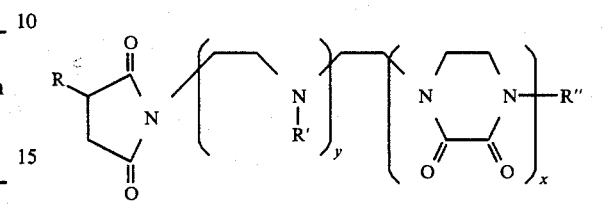

in which R is a hydrocarbyl radical having from 8 to 400 carbon atoms, x and y are numbers which range from 0 to 6 whose additive total is from 1 to 6 and which can be the same or different, R' is a hydrogen radical or a mono- or bi-acyl radical of oxalic acid, and R" is a hydrogen or hydrocarbyl substituted succinic-N-ethylene radical of the formula:

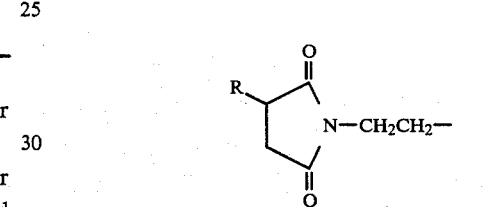

Wherein from about 40 to 100 wt% of said detergent compound is the oxalic acid derivative of mono-succinimide and the remainder comprises the oxalic acid derivative of bis-succinimide.

2. The fuel composition of claim 1 containing from about 10 to 200 pounds of said additive per thousand barrels of fuel.

3. The fuel of claim 1 wherein said compound has R with 16 carbon atoms, x is 0, y is 6, R' and R" are hydrogen.

4. The fuel of claim 1, wherein said compound has R with 32 carbon atoms, x is 6, y is 0, R' and R" are hydrogen.

5. The fuel of claim 1, wherein said compound has R with 200 atoms, x is 3, y is 3, R' is mono-oxalyl and R" is alkenyl succinyl-N-ethylenyl.

6. The fuel of claim 1, wherein said compound has R with 400 carbon atoms, x is 2, y is 4, R' is bis-oxalyl and R" is alkenyl succinyl-N-ethylenyl.

7. The fuel of claim 1, wherein said compound has R with 8 carbon atoms, x is 5, y is 1, R' is mono-oxalyl and R" is hydrogen.

* * * * *